(12) United States Patent
Song

(10) Patent No.: US 7,846,383 B2
(45) Date of Patent: Dec. 7, 2010

(54) LATERAL FLOW ASSAY DEVICE AND ABSORBENT ARTICLE CONTAINING SAME

(75) Inventor: Xuedong Song, Roswell, GA (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 1026 days.

(21) Appl. No.: 11/640,116

(22) Filed: Dec. 15, 2006

(65) Prior Publication Data

US 2008/0145945 A1    Jun. 19, 2008

(51) Int. Cl.
*G01N 33/00* (2006.01)

(52) U.S. Cl. .......................... 422/58; 422/68.1; 422/99; 422/102; 436/97

(58) Field of Classification Search ................ 422/58, 422/68.1, 99, 102; 436/97
See application file for complete search history.

(56) References Cited

U.S. PATENT DOCUMENTS

| | | |
|---|---|---|
| 3,446,599 A | 5/1969 | Shand |
| 3,630,680 A | 12/1971 | Rittersdorf et al. |
| 3,712,853 A | 1/1973 | Rittersdorf et al. |
| 3,802,842 A | 4/1974 | Lange et al. |
| 3,814,586 A | 6/1974 | Fraser, Jr. et al. |
| 3,850,576 A | 11/1974 | Rittersdorf et al. |
| 3,853,466 A | 12/1974 | Rittersdorf et al. |
| 3,853,471 A | 12/1974 | Rittersdorf et al. |
| 3,853,472 A | 12/1974 | Rittersdorf et al. |
| 3,853,476 A | 12/1974 | Rittersdorf et al. |
| 3,880,588 A | 4/1975 | Rittersdorf et al. |
| 3,989,462 A | 11/1976 | Hirsch |
| 4,013,416 A | 3/1977 | Rittersdorf et al. |
| 4,158,546 A | 6/1979 | Lam et al. |
| 4,161,507 A | 7/1979 | Hirsch |

(Continued)

FOREIGN PATENT DOCUMENTS

DE    4403437 A1    8/1995

(Continued)

OTHER PUBLICATIONS

Article—Macroscopic Urinalysis (Chemstrip 10) Universtiy of Michigan, http://www.pathology.med.umich.edu/poc/onsite/poc-chemstrip-10.html, Nov. 15, 2006.

(Continued)

*Primary Examiner*—Sam P Siefke
(74) *Attorney, Agent, or Firm*—Dority & Manning, P.A.

(57) ABSTRACT

A lateral flow assay device for testing a bodily fluid, such as urine, blood, mucous, saliva, etc., is provided. The lateral flow assay device includes a chromatographic medium (e.g., porous membrane) that defines a detection zone that provides a signal indicative of the presence or amount of bilirubin or urobilinogen. The device may also include a control zone that provides a signal indicative of whether a sufficient amount of bodily fluid has been provided and tested. In one embodiment, the device is integrated into an absorbent article to provide a user or caregiver with rapid information about a health condition. For example, the device may be integrated into a diaper to provide information about the presence of bilirubin and/or urobilinogen. This information may provide an early warning system to allow the user or caregiver to seek additional testing and/or treatment. Alternatively, semi-quantitative or quantitative results may be derived from the test.

47 Claims, 4 Drawing Sheets

U.S. PATENT DOCUMENTS

| | | |
|---|---|---|
| 4,190,419 A | 2/1980 | Bauer |
| 4,290,771 A | 9/1981 | Hirsch |
| 4,345,911 A | 8/1982 | Kohl |
| 4,385,114 A | 5/1983 | Güthlein et al. |
| 4,665,038 A | 5/1987 | Sakata et al. |
| 4,703,017 A | 10/1987 | Campbell et al. |
| 4,704,116 A | 11/1987 | Enloe |
| 4,738,674 A | 4/1988 | Todd et al. |
| 4,742,011 A | 5/1988 | Blake et al. |
| 4,743,560 A | 5/1988 | Campbell et al. |
| 4,835,099 A | 5/1989 | Mize et al. |
| 4,855,240 A | 8/1989 | Rosenstein et al. |
| 4,889,816 A | 12/1989 | Davis et al. |
| 4,904,583 A | 2/1990 | Mapes et al. |
| 4,916,056 A | 4/1990 | Brown, III et al. |
| 4,920,045 A | 4/1990 | Okuda et al. |
| 4,954,435 A | 9/1990 | Krauth |
| 4,956,302 A | 9/1990 | Gordon et al. |
| 4,978,625 A | 12/1990 | Wagner et al. |
| 4,980,298 A | 12/1990 | Blake et al. |
| 5,073,340 A | 12/1991 | Covington et al. |
| 5,075,077 A | 12/1991 | Durley, III et al. |
| 5,075,078 A | 12/1991 | Osikowicz et al. |
| 5,120,643 A | 6/1992 | Ching et al. |
| 5,149,622 A | 9/1992 | Brown et al. |
| 5,185,127 A | 2/1993 | Vonk |
| 5,192,606 A | 3/1993 | Proxmire et al. |
| 5,208,143 A | 5/1993 | Henderson et al. |
| 5,244,631 A | 9/1993 | Morikawa |
| 5,252,459 A | 10/1993 | Tarcha et al. |
| 5,275,785 A | 1/1994 | May et al. |
| 5,399,219 A | 3/1995 | Roessler et al. |
| 5,428,690 A | 6/1995 | Bacus et al. |
| 5,468,236 A | 11/1995 | Everhart et al. |
| 5,486,166 A | 1/1996 | Bishop et al. |
| 5,490,846 A | 2/1996 | Ellis et al. |
| 5,504,013 A | 4/1996 | Senior |
| 5,540,796 A | 7/1996 | Fries |
| 5,573,919 A | 11/1996 | Kearns et al. |
| 5,591,645 A | 1/1997 | Rosenstein |
| 5,595,618 A | 1/1997 | Fries et al. |
| 5,599,661 A | 2/1997 | Senba et al. |
| 5,602,040 A | 2/1997 | May et al. |
| 5,613,077 A | 3/1997 | Leung et al. |
| 5,622,871 A | 4/1997 | May et al. |
| 5,656,503 A | 8/1997 | May et al. |
| 5,670,381 A | 9/1997 | Jou et al. |
| 5,702,377 A | 12/1997 | Collier, IV et al. |
| 5,714,389 A | 2/1998 | Charlton et al. |
| 5,736,408 A | 4/1998 | Carter et al. |
| 5,788,863 A | 8/1998 | Milunic |
| 5,798,273 A | 8/1998 | Shuler et al. |
| 5,931,823 A | 8/1999 | Stokes et al. |
| 5,945,281 A | 8/1999 | Prabhu |
| 5,955,374 A | 9/1999 | Smith et al. |
| 5,989,924 A | 11/1999 | Root et al. |
| 5,989,926 A | 11/1999 | Bradley et al. |
| 5,998,221 A | 12/1999 | Malick et al. |
| 6,057,165 A | 5/2000 | Mansour |
| 6,060,638 A | 5/2000 | Paul et al. |
| 6,077,669 A | 6/2000 | Little et al. |
| 6,130,100 A | 10/2000 | Jobling et al. |
| 6,133,048 A | 10/2000 | Penfold et al. |
| 6,150,002 A | 11/2000 | Varona |
| 6,156,271 A | 12/2000 | May |
| 6,187,269 B1 | 2/2001 | Lancesseru et al. |
| 6,194,220 B1 | 2/2001 | Malick et al. |
| 6,203,496 B1 | 3/2001 | Gael et al. |
| 6,234,241 B1 | 5/2001 | Elmore |
| 6,274,324 B1 | 8/2001 | Davis et al. |
| 6,294,391 B1 | 9/2001 | Bradley et al. |
| 6,399,398 B1 | 6/2002 | Cunningham et al. |
| 6,464,635 B1 | 10/2002 | Jimenez Cerrato et al. |
| 6,515,194 B2 | 2/2003 | Neading et al. |
| 6,524,864 B2 | 2/2003 | Fernandez de Castro |
| 6,627,459 B1 | 9/2003 | Tung et al. |
| 6,653,149 B1 | 11/2003 | Tung et al. |
| 6,663,611 B2 | 12/2003 | Blaney et al. |
| 6,669,908 B2 | 12/2003 | Weyker et al. |
| 6,689,617 B1 | 2/2004 | Abels |
| 6,713,660 B1 | 3/2004 | Roe et al. |
| 6,777,243 B2 | 8/2004 | Fukuoka et al. |
| 6,951,631 B1 | 10/2005 | Catt et al. |
| 7,044,919 B1 | 5/2006 | Catt et al. |
| 7,052,831 B2 | 5/2006 | Fletcher et al. |
| 2002/0042149 A1 | 4/2002 | Butilin et al. |
| 2002/0045273 A1 | 4/2002 | Butlin et al. |
| 2003/0119202 A1 | 6/2003 | Kaylor et al. |
| 2003/0119204 A1 | 6/2003 | Wei et al. |
| 2003/0124739 A1 | 7/2003 | Song et al. |
| 2003/0158530 A1 | 8/2003 | Diehl et al. |
| 2004/0102750 A1 | 5/2004 | Jameson |
| 2004/0121334 A1 | 6/2004 | Wei et al. |
| 2004/0121480 A1 | 6/2004 | Wei et al. |
| 2004/0151632 A1 | 8/2004 | Bradley et al. |
| 2004/0161859 A1 | 8/2004 | Guo et al. |
| 2005/0029924 A1 | 2/2005 | Okay et al. |
| 2005/0036148 A1 | 2/2005 | Phelan et al. |
| 2005/0037510 A1 | 2/2005 | Sharrock et al. |
| 2005/0054255 A1 | 3/2005 | Morman et al. |
| 2005/0059941 A1 | 3/2005 | Baldwin et al. |
| 2005/0109951 A1 | 5/2005 | Fish et al. |
| 2005/0112635 A1 | 5/2005 | Gentle et al. |
| 2005/0112779 A1 | 5/2005 | Wei et al. |
| 2005/0112780 A1 | 5/2005 | Song |
| 2005/0191704 A1 | 9/2005 | Boga et al. |
| 2006/0025732 A1 | 2/2006 | Ying et al. |
| 2006/0127886 A1 | 6/2006 | Kaylor et al. |
| 2006/0127924 A1 | 6/2006 | Hellyer et al. |
| 2006/0223193 A1 | 10/2006 | Song et al. |
| 2006/0240569 A1 | 10/2006 | Goldenbaum et al. |
| 2006/0246601 A1 | 11/2006 | Song et al. |
| 2007/0048807 A1 | 3/2007 | Song |

FOREIGN PATENT DOCUMENTS

| | | |
|---|---|---|
| EP | 1034758 A1 | 9/2000 |
| GB | 2183160 A | 6/1987 |
| WO | WO 9516425 A1 | 6/1995 |
| WO | WO 0065348 A2 | 11/2000 |
| WO | WO 0065348 A3 | 11/2000 |
| WO | WO 0113109 A2 | 2/2001 |
| WO | WO 0113109 A3 | 2/2001 |
| WO | WO 2006118622 A1 | 11/2006 |

OTHER PUBLICATIONS

Research Article—Analysis of formaldehyde in the headspace of urine from bladder and prostate cancer patients using selected iron tube mass spectrometry, Rapid Commun. Mass Spectrom.,1999; 13;1354-9.

Research Artice—Selective measurement of HCHO in urine direct liquid-phase fluorimetric analysis, Clin. Chem. Lab. Med. 1005; 42(2); 178-182.

Boga et al., U.S. Appl. No. 11/638,760, filed Dec. 14, 2006, Detection of Formaldehyde in Urine Samples.

Xuedong Song, U.S. Appl. No. 11/217,097, filed Aug. 31, 2005, Enzyme Detection Technique.

Song et al., U.S. Appl. No. 11/217,099, filed Aug. 31, 2005, Nitrite Detection Technique.

Xuedong Song, U.S. Appl. No. 11/589,671, filed Oct. 30, 2006, Absorbent Article Containing Lateral Flow Assay Device.

Song et al., U.S. Appl. No. 11/640,100, filed Dec. 15, 2006, Indicator Immobilization on Assay Device.

Search Report and Written Opinion for PCT/IB2007/053963 dated Jun. 25, 2008.

Alan Weiss, Concurrent engineering for lateral-flow diagnostics, *IVD Technology Magazine*, Nov./Dec. 1999, 8 pages.

LATERAL FLOW ASSAY DEVICE AND ABSORBENT ARTICLE CONTAINING SAME

BACKGROUND

Multiple tests have been developed for detecting components in urine. Such tests can provide information about overall health as well as provide an indication of a specific health problem. When timely administered, such tests may also be able to provide an early indication of a health problem, which may be very advantageous for effective treatment. By way of example, urine testing can be used to detect jaundice prior to visible symptoms. Jaundice is typically caused by increased levels of bilirubin in the body. Increased levels of bilirubin as well as the reduction products of bilirubin, e.g., urobilinogen, can be an indicator of several disease states including, for instance, malaria, sickle cell anemia, hepatitis B, hepatitis C, hepatotoxicity, alcoholism, cirrhosis, Gilbert's syndrome, gallstones, and cancers including pancreatic cancer, ductal carcinoma as well as metastatic carcinomas in general.

Such tests may be performed by having a patient voluntarily collect and provide a sample. However, patient-collected urine samples may not be readily available with certain test subjects such as children, elderly adults, and injured or non-ambulatory patients. Additionally, it may be preferable to collect and test urine samples from these subjects at certain times or conditions where the patient is not necessarily in the presence of medical or otherwise specially trained personnel. Frequently, such subjects may be provided with a diaper or other absorbent article to collect urine and provide for disposal in a hygienic manner. Of course, these articles must be periodically checked to determine whether urine and other bodily waste have been collected.

Specific products have been developed for collecting and detecting urine samples using a diaper and/or an absorbent article. By way of example, U.S. Pat. No. 6,713,660 describes a disposable article that includes a biosensor adapted to detect a specific biological analyte in bodily waste. U.S. Pat. No. 6,203,496 indicates a disposable diaper having one or more chemical reagents applied to the absorbent region that change color when certain components are present. U.S. Pat. No. 5,468,236 indicates a disposable absorbent product that includes a chemically reactive means that is applied, for example, to one or more layers of the absorbent product.

Despite these developments, a need for improvement remains. A device capable of testing a bodily fluid such as urine for one or more particular components symptomatic of jaundice or liver disease would be beneficial. Additionally, an absorbent article that can provide, an effective urine test for early detection of analytes symptomatic of jaundice would also be particularly beneficial.

SUMMARY

In accordance with one embodiment, a diagnostic test kit for detecting the presence or amount of bilirubin and/or urobilinogen within a test sample is disclosed. The test kit comprises indicator, e.g., a diazonium ion or an Ehrlich reagent (p-aminobenzaldehyde and its derivatives) that may react with bilirubin or urobilinogen. The device also comprises a lateral flow assay device that includes a chromatographic medium and an absorbent material that receives the test sample after flowing through the chromatographic medium. The chromatographic medium defines a detection zone within which the indicator may be immobilized and exhibit a color change upon reaction with the targeted analyte, i.e., bilirubin or a reduction product of bilirubin.

In accordance with another embodiment, disclosed is an absorbent article for receiving a bodily fluid suspected of containing bilirubin or urobilinogen in levels associated with jaundice. The article comprises a substantially liquid impermeable layer; a liquid permeable layer; an absorbent core positioned between the substantially liquid impermeable layer and the liquid permeable layer; and a lateral flow assay device integrated into the article and positioned such that the device is in fluid communication with the bodily fluid when provided by a wearer of the article. The lateral flow assay device comprises a chromatographic medium that defines a detection zone, the detection zone being configured for exhibiting a signal indicative of the presence or amount of bilirubin and/or urobilinogen in the bodily fluid.

In accordance with another embodiment, a method of detecting the presence of bilirubin or a reduction product of bilirubin within a bodily fluid is disclosed. The method comprises providing a lateral flow assay device, the lateral flow assay device comprising a chromatographic medium that defines a detection zone, the detection zone being configured to provide a visual detection signal indicative of the presence or amount of bilirubin or urobilinogen within the bodily fluid. The lateral flow assay device is contacted with the bodily fluid, and the detection zone is observed for the visual detection signal.

BRIEF DESCRIPTION OF THE DRAWINGS

A full and enabling disclosure of the present subject matter, including the best mode thereof, directed to one of ordinary skill in the art, is set forth more particularly in the remainder of the specification, which makes reference to the appended figures in which.

Figure 1:
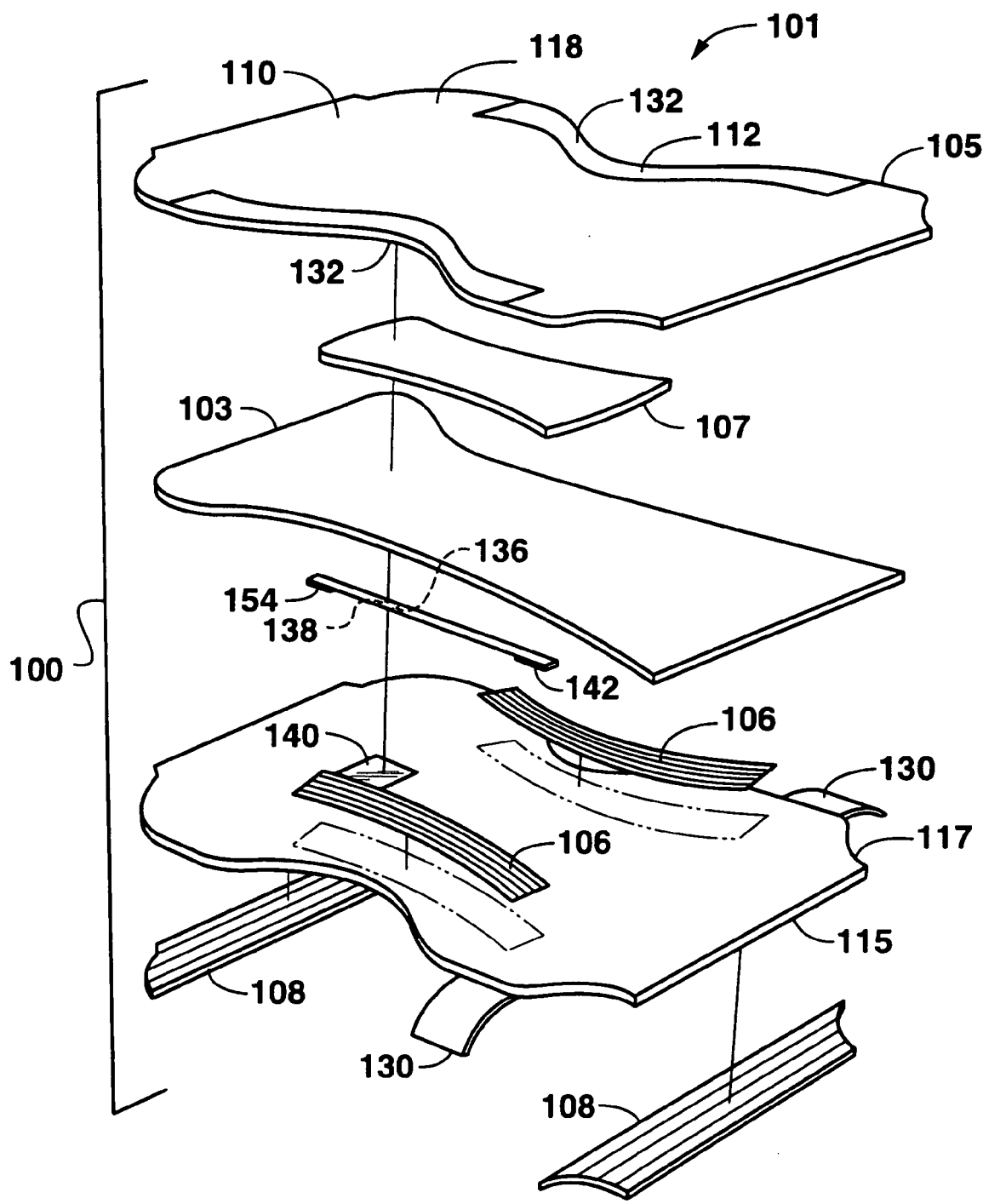
FIG. 1 is an exploded view of an exemplary embodiment.

Repeat use of reference characters in the present specification and drawings is intended to represent same or analogous features or elements of the disclosed subject matter.

DETAILED DESCRIPTION OF REPRESENTATIVE EMBODIMENTS

Reference now will be made in detail to various embodiments of the disclosed subject matter, one or more examples of which are set forth below. Each example is provided by way of explanation, not limitation of the subject matter. In fact, it will be apparent to those skilled in the art that various modifications and variations may be made without departing from the scope or spirit of the disclosure. For instance, features illustrated or described as part of one embodiment, may be used on another embodiment to yield a still further embodiment. Thus, it is intended that the present disclosure cover such modifications and variations.

Generally speaking, the present disclosure is directed to a diagnostic test kit for testing a bodily fluid, such as urine, blood, mucous, saliva, etc. The diagnostic test kit includes a lateral flow assay device including a chromatographic medium (e.g., porous membrane) that defines a detection zone that provides a signal indicative of the presence or absence of bilirubin or urobilinogen, a reduction product of bilirubin. The lateral flow device may also include additional zones such as a reagent zone that provides components such as buffers to provide a pH environment to encourage development of the signal, surfactants, and the like and/or a control zone that provides a signal indicative of whether a sufficient amount of bodily fluid has been provided for testing.

In one embodiment, a lateral flow assay device is integrated into an absorbent article, e.g., a diaper, to provide a user or caregiver with rapid information about a health condition. For example, a lateral flow device may be integrated into a diaper to provide information concerning compounds often encountered with diseases associated with jaundice. This information may provide an early warning system to allow the user or caregiver to seek additional testing and/or treatment. Alternatively, semi-quantitative or quantitative results may be derived from the test.

Various embodiments will now be described in more detail.

I. Lateral Flow Assay Device

Generally speaking, a lateral flow assay device is employed to perform a heterogeneous assay for one or more analytes common in jaundice, e.g., bilirubin and urobilinogen. A heterogeneous assay is one in which a species is separated from another species prior to detection. Separation may be carried out by physical separation, e.g., by transferring one of the species to another reaction vessel, filtration, centrifugation, chromatography, solid phase capture, magnetic separation, and so forth. The separation may also be nonphysical in that no transfer of one or both of the species is conducted, but the species are separated from one another in situ.

Figure 6:
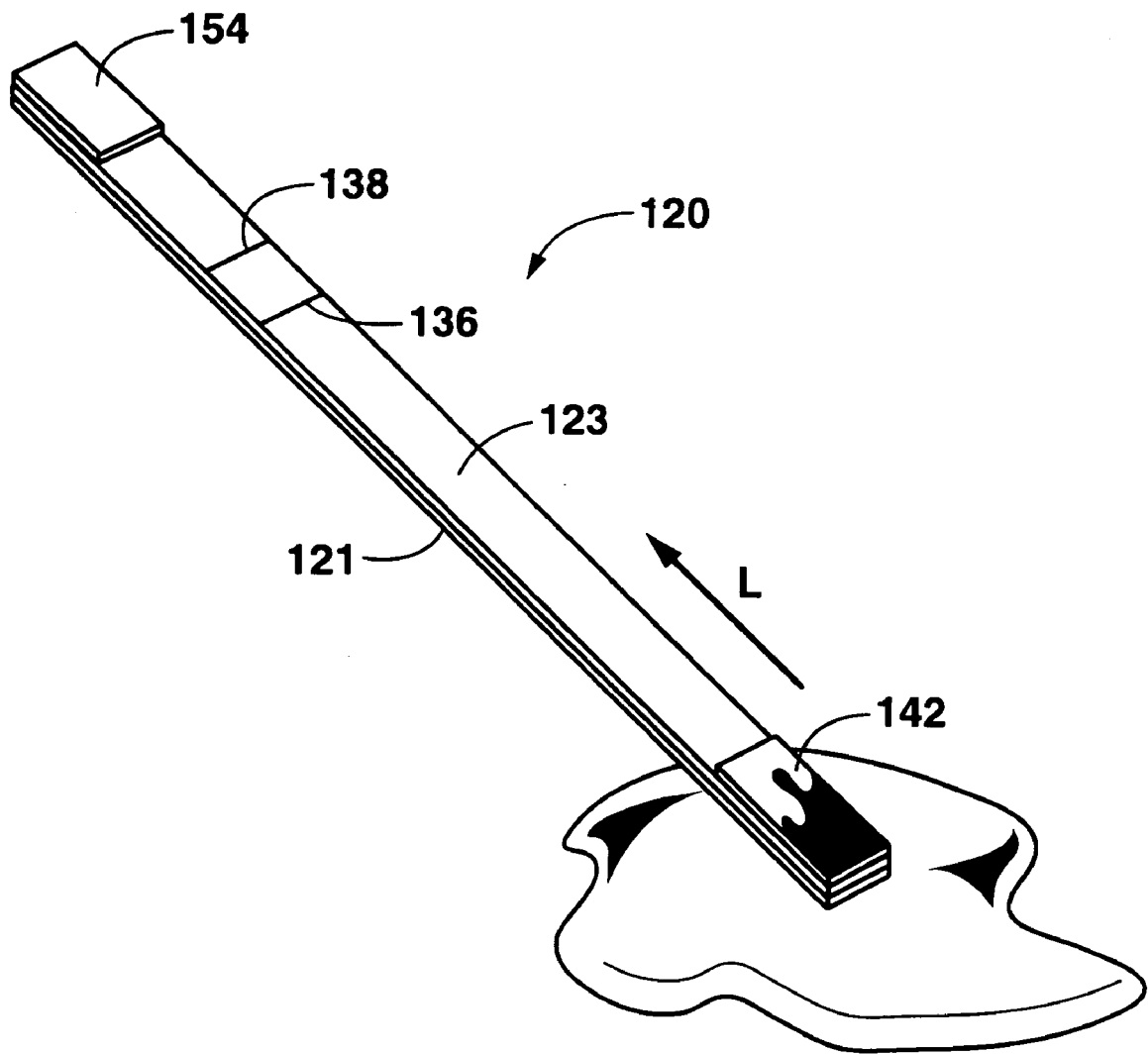
FIG. 6 is a perspective view that provides an example of a lateral flow assay device as may be used in certain exemplary embodiments.

In any event, the use of a lateral flow assay device provides a variety of benefits, including a more uniform flow of the bodily fluid and reagents during testing. This may enhance the accuracy of the test and minimize the need for external control mechanisms. Referring to FIG. 6, for example, one embodiment of a lateral flow assay device 120 will now be described in more detail. As shown, the device 120 contains a chromatographic medium 123 optionally supported by a rigid support 121. The chromatographic medium 123 may be made from any of a variety of materials through which the test sample is capable of passing. For example, the chromatographic medium 123 may be a porous membrane formed from synthetic or naturally occurring materials, such as polysaccharides (e.g., cellulose materials such as paper and cellulose derivatives, such as cellulose acetate and nitrocellulose); polyether sulfone; polyethylene; nylon; polyvinylidene fluoride (PVDF); polyester; polypropylene; silica; inorganic materials, such as deactivated alumina, diatomaceous earth, $MgSO_4$, or other inorganic finely divided material uniformly dispersed in a porous polymer matrix, with polymers such as vinyl chloride, vinyl chloride-propylene copolymer, and vinyl chloride-vinyl acetate copolymer; cloth, both naturally occurring (e.g., cofton) and synthetic (e.g., nylon or rayon); porous gels, such as silica gel, agarose, dextran, and gelatin; polymeric films, such as polyacrylamide; and so forth. In one particular embodiment, the chromatographic medium 123 is formed from nitrocellulose and/or polyether sulfone materials. It should be understood that the term "nitrocellulose" refers to nitric acid esters of cellulose, which may be nitrocellulose alone, or a mixed ester of nitric acid and other acids, such as aliphatic carboxylic acids having from 1 to 7 carbon atoms.

The size and shape of the chromatographic medium 123 may generally vary as is readily recognized by those skilled in the art. For instance, a porous membrane strip may have a length of from about 10 to about 100 millimeters, in some embodiments from about 20 to about 80 millimeters, and in some embodiments, from about 40 to about 60 millimeters. The width of the membrane strip may also range from about 0.5 to about 20 millimeters, in some embodiments from about 1 to about 15 millimeters, and in some embodiments, from about 2 to about 10 millimeters. Likewise, the thickness of the membrane strip is generally small enough to allow transmission-based detection. For example, the membrane strip may have a thickness less than about 500 micrometers, in some embodiments less than about 250 micrometers, and in some embodiments, less than about 150 micrometers.

As stated above, the support 121 carries the chromatographic medium 123. For example, the support 121 may be positioned directly adjacent to the chromatographic medium 123 as shown in FIG. 6, or one or more intervening layers may be positioned between the chromatographic medium 123 and the support 121. Regardless, the support 121 may generally be formed from any material able to carry the chromatographic medium 123. The support 121 may be formed from a material that is transmissive to light, such as transparent or optically diffuse (e.g., translucent) materials. Also, it may be desired that the support 121 is liquid-impermeable so that fluid flowing through the medium 123 does not leak through the support 121. Examples of suitable materials for the support include, but are not limited to, glass; polymeric materials, such as polystyrene, polypropylene, polyester (e.g., Mylar® film), polybutadiene, polyvinylchloride, polyamide, polycarbonate, epoxides, methacrylates, and polymelamine; and so forth. To provide a sufficient structural backing for the chromatographic medium 123, the support 121 is generally selected to have a certain minimum thickness. Likewise, the thickness of the support 121 is typically not so large as to adversely affect its optical properties. Thus, for example, the support 121 may have a thickness that ranges from about 100 to about 5,000 micrometers, in some embodiments from about 150 to about 2,000 micrometers, and in some embodiments, from about 250 to about 1,000 micrometers. For instance, one suitable membrane strip having a thickness of about 125 micrometers may be obtained from Millipore Corp. of Bedford, Mass. under the name "SHF180UB25."

The chromatographic medium 123 may be cast onto the support 121, wherein the resulting laminate may be die-cut to the desired size and shape. Alternatively, the chromatographic medium 123 may simply be laminated to the support 121 with, for example, an adhesive. In some embodiments, a nitrocellulose or nylon porous membrane is adhered to a Mylar® film. An adhesive is used to bind the porous membrane to the Mylar® film, such as a pressure-sensitive adhesive. Laminate structures of this type are believed to be commercially available from Millipore Corp. of Bedford, Mass. Still other examples of suitable laminate device structures are described in U.S. Pat. No. 5,075,077 to Durley, III, et al., which is incorporated herein in its entirety by reference thereto for all purposes.

The device 120 may also contain an absorbent material 154 that is positioned adjacent to the medium 123. The absorbent material 154 assists in promoting capillary action and fluid flow through the medium 123. In addition, the absorbent material 154 receives fluid that has migrated through the entire chromatographic medium 123 and thus draws any unreacted components away from the detection region to help reduce the likelihood of "false positives." Some suitable absorbent materials that may be used include, but are not limited to, nitrocellulose, cellulosic materials, porous polyethylene pads, glass fiber filter paper, and so forth. The absorbent material may be wet or dry prior to being incorporated into the device. Pre-wetting may facilitate capillary flow for some fluids, but is not typically required. Also, as is well known in the art, the absorbent material may be treated with a surfactant to assist the wicking process.

To initiate the detection of an analyte, the bodily fluid (e.g., urine) may be applied to a portion of the chromatographic medium 123 through which it may then travel in the direction illustrated by arrow "L" in FIG. 6. Alternatively, the fluid may first contact a sample application zone 142 that is in fluid communication with the chromatographic medium 123. The sample application zone 142 may be defined by a separate pad or material as shown in FIG. 6, or simply defined by the chromatographic medium 123. In the illustrated embodiment, the fluid may travel from the sample application zone 142 to a reagent pad (not shown) that may be placed in communication with one end of the sample pad. The reagent pad may contain one or more diffusively immobilized reagents and may be formed from a material through which a fluid is capable of passing (e.g., glass fibers). Some suitable materials that may be used to form the absorbent material 154 and/or sample pad include, but are not limited to, nitrocellulose, cellulose, porous polyethylene pads, and glass fiber filter paper. If desired, the sample pad may also contain one or more assay pretreatment reagents, either diffusively or non-diffusively attached thereto.

The lateral flow assay device employs one or more zones for providing an indication of the presence of bilirubin and/or urobilinogen. More specifically, such zone(s) typically contain a chemical or biological reagent that interacts with the bilirubin or urobilinogen and/or other reagents to generate a signal (e.g., visual signal). Referring again to FIG. 6, for example, the lateral flow assay device 120 includes a detection zone 136 within which an indicator is disposed.

The specific reagents employed in the lateral flow assay device include those capable of directly detecting the presence of bilirubin and/or urobilinogen, for instance, as an early diagnosis of jaundice. Although bilirubin is normally present in the blood in a range of between about 0.2 and about 1.5 mg/dl, it is not normally present in urine. Urobilinogen, on the other hand, is not normally found in blood, but small amounts may be normally detected in urine. Hence, bilirubin and/or urobilinogen can be used as biomarkers for the early detection of disease.

A variety of indicator reagents may be used for detecting the presence of bilirubin and/or urobilinogen. One such indicator is a detection reagent that is chemically acted upon by bilirubin or urobilinogen to form a detectable dye. For example, the indicator reagent may be a diazonium salt that reacts with bilirubin or urobilinogen to form an azo dye. Bilirubin and urobilinogen are capable of undergoing electrophilic attack by a diazonium ion having the generic formula:

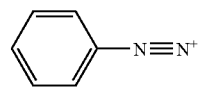

The diazonium ion may be zwitterionic in that the counterion of the diazonium moiety is covalently bound to the ring system. The ring system of the diazonium ion may be substituted or unsubstituted. The ion may be provided by a variety of suitable diazonium salts, such as diazonium chlorides, diazonium acid sulphates, diazonium alkyl sulphates, diazonium fluoborates, diazonium benzenesulphonates, diazonium acid 1,5-naphthalenedisulphonates, and so forth.

As indicated above, bilirubin or urobilinogen is capable of undergoing electrophilic attack by an indicator reagent (e.g., diazonium ion). This reaction is often referred to as "coupling" and results in the formation of a product having a color different from that of the starting indicator reagent. For example, diazonium ions may react with aromatic compounds to form an aromatic azo compound having the generic formula, R—N=N—R', wherein "R" and "R'" are aryl groups. Without intending to be limited by theory, it is believed that this reaction induces either a shift of the absorption maxima towards the red end of the spectrum ("bathochromic shift") or towards the blue end of the spectrum ("hypsochromic shift"). The type of absorption shift depends on the nature of the resulting azo molecule and whether it functions as an electron acceptor (oxidizing agent), in which a hypsochromic shift results, or whether it functions as an electron donor (reducing agent), in which a bathochromic shift results. The absorption shift provides a color difference that is detectable, either visually or through instrumentation, to indicate the presence of the analyte, i.e., bilirubin or urobilinogen, within the test sample. For example, prior to contact with an infected test sample, the diazonium ion may be colorless or it may possess a certain color. However, after contacting the test sample and reacting with bilirubin, an aromatic azo compound will form that exhibits a color that is different than the initial color of the diazonium ion.

The diazonium salt may be selected to preferentially bind to a particular analyte. For example, a non-limiting listing of diazonium compounds suitable for use in the detection of bilirubin may include p-aminobenzenesulfonic acid, 2,6-dichlorobenzene diazonium tetrafluoroborate, 2-trifluoromethylbenzene diazonium.

Diazonium ions which preferentially couple urobilinogen may include those having the following general structure:

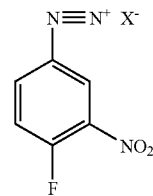

In which X⁻ represents a stabilizing anion.

In another embodiment, a diazonium ion having the following general structure can be used for the preferential detection of urobilinogen:

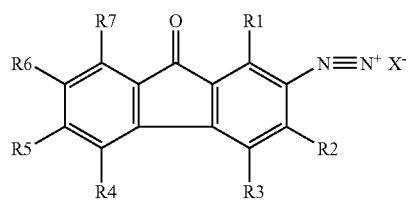

wherein R1 through R7 are independently a hydrogen atom, a halogen atom, a lower alkyl group or a lower alkoxy group; and X is a stabilizing anion.

A non-limiting listing of diazonium compounds that may be utilized to preferentially couple urobilinogen may include 4-fluoro-3-nitrobenzenediazonium salt, 4-methoxybenzenediazonium-tetrafluoroborate, 3,3'-dimethoxybiphenyl-4,4'-diazonium salt, and the like.

Of course, indicators other than diazonium salts may be used to provide a detectable signal in the presence of bilirubin and/or urobilinogen. For example, Erhlich reagents and derivatives thereof may be used in the detection of urobilinogen in a test sample. Erhlich reagents are small molecular p-aminobenzaldehyde molecules that may preferentially react with urobilinogen. Similar to diazonium compounds, Erhlich reagents react with urobilinogen to produce a detectable color change. Erhlich reagents for use in the disclosed products can include, without limitation, dialkylaminbenzaldehydes such as dimethylaminobenzaldehyde and diethylaminobenzaldehyde.

Referring again to FIG. 6, the indicator reagent may be disposed downstream from the sample application zone 142. For instance, an above-described indicator reagent may be immobilized within the detection zone 136 of the lateral flow assay device 120. For example, a diazonium ion may be applied directly to the medium 123 or first formed into a solution prior to application. Various solvents may be utilized to form the solution, such as, but not limited to, acetonitrile, dimethylsulfoxide (DMSO), ethyl alcohol, dimethylformamide (DMF), and other polar organic solvents. For instance, the amount of a diazonium salt in the solution may range from about 0.001 to about 100 milligrams per milliliter of solvent, and in some embodiments, from about 0.1 to about 10 milligrams per milliliter of solvent. In one particular embodiment, the detection zone 136 is defined by the chromatographic medium 123 and formed by non-diffusively immobilizing the indicator thereon using well-known techniques and then dried. The indicator reagent concentration may be selectively controlled to provide the desired level of detection sensitivity.

In general, the indicator reagent may be applied in a manner so that it does not substantially diffuse through the matrix of the chromatographic medium 123 (i.e., non-diffusively immobilized). This enables a user to readily detect the change in color that occurs upon reaction of the indicator with the analyte. In this regard, certain macromolecular reagents (e.g., polymers, oligomers, dendrimers, particles, etc.) may be particularly useful in the device. Generally speaking, such macromolecular reagents contain at least two functionalities, i.e., a reactive moiety and a macromolecular moiety, which are covalently or noncovalently joined. The macromolecular moiety may include, for instance, a polymeric moiety, such as a linear or branched, homopolymer or copolymer. The polymeric moieties may be natural, synthetic, or combinations thereof. Examples of natural polymeric moieties include, for instance, peptides, proteins, DNA/RNA and polysaccharides (e.g., glucose-based polymers). Examples of synthetic polymeric moieties include, instance, polyacrylic acid and polyvinyl alcohols. One particular example of a suitable polysaccharide detection reagent is activated dextran (polymeric moiety) conjugated to dichlorobenzene diazonium tetrafluoroborate (diazonium moiety).

As indicated, the macromolecular moiety may also be a particle (sometimes referred to as a "bead" or "microbead"). Naturally occurring particles, such as nuclei, mycoplasma, plasmids, plastids, mammalian cells (e.g., erythrocyte ghosts), unicellular microorganisms (e.g., bacteria), polysaccharides (e.g., agarose), etc., may be used. Further, synthetic particles may also be utilized. For example, in one embodiment, latex microparticles may be utilized. Although any synthetic particle may be used, the particles are typically formed from polystyrene, butadiene styrenes, styreneacrylicvinyl terpolymer, polymethylmethacrylate, polyethylmethacrylate, styrene-maleic anhydride copolymer, polyvinyl acetate, polyvinylpyridine, polydivinylbenzene, polybutyleneterephthalate, acrylonitrile, vinylchloride-acrylates, and so forth, or an aldehyde, carboxyl, amino, hydroxyl, or hydrazide derivative thereof. When utilized, the shape of the particles may generally vary. In one particular embodiment, for instance, the particles are spherical in shape. However, it should be understood that other shapes are also contemplated by the present invention, such as plates, rods, discs, bars, tubes, irregular shapes, etc. In addition, the size of the particles may also vary. For instance, the average size (e.g., diameter) of the particles may range from about 0.1 nanometers to about 1,000 microns, in some embodiments, from about 0.1 nanometers to about 100 microns, and in some embodiments, from about 1 nanometer to about 10 microns.

The particle may generally be joined to an indicator using any of a variety of well-known techniques. For instance, covalent attachment of a particle to an indicator reagent may be accomplished using carboxylic, amino, aldehyde, bromoacetyl, iodoacetyl, thiol, epoxy or other reactive functional groups, as well as residual free radicals and radical cations, through which a coupling reaction may be accomplished. A surface functional group may also be incorporated as a functionalized co-monomer because the surface of the particle may contain a relatively high surface concentration of polar groups. In certain cases, the particle may be capable of direct covalent bonding to an indicator reagent without the need for further modification. It should also be understood that, besides covalent bonding, other attachment techniques, such as physical adsorption, may also be utilized in the present invention.

In one particular embodiment, a particle carrying the Erhlich reagent moieties (p-aminobenzaldehyde) may be non-diffusively bound to the chromatographic medium 123 at the detection zone 136. Following application of a test sample, urobilinogen in the sample may interact with the Erhlich reagent and provide a detectable signal at the detection zone.

One benefit of the lateral flow assay device is its ability to readily incorporate one or more additional zones to facilitate the desired reactions. By way of example, a reagent zone (not shown) may be utilized. In the illustrated embodiment, the reagent zone may be located such that test sample travels from the sample application zone 142 to a reagent zone that is in fluid communication with the sample application zone 142. The reagent zone may be formed on the medium 123. Alternatively, the reagent zone may be formed from a separate material or pad. Such a reagent pad may be formed from any material through which the test sample is capable of passing, such as glass fibers. Reagents that may facilitate the coupling reactions, can include, for instance, surfactants, stabilizers, and the like, that may be diffusively or non-diffusively immobilized in a reagent zone.

In one embodiment, reagents that may be used to facilitate detection of bilirubin and/or urobilinogen may include buffers. For example, urobilinogen reactions with Erhlich reagent-based indicators generally take place in an acidic medium. Accordingly, the pH of a test sample may be adjusted by inclusion of a suitable buffer to a relatively acidic level to facilitate the desired coupling reaction. Acidic buffers can include, for instance, metaphosphoric acid, citric acid, oxalic acid, boric acid, and the like. Typically, to accomplish the desired pH level, the buffer may be diffusively immobilized on the lateral flow assay device 120. For example, a buffer may be mixed with the indicator reagent prior to application to the device 120 and applied in conjunction with the indicator reagent at the detection zone 136. Alternatively, the buffer may be separately applied to the lateral flow assay device 120 so that it mixes with the test sample upon exposure to the bodily fluid being tested and prior to exposure to the indicator reagent.

In one embodiment, a buffer can be diffusively immobilized at or upstream of a detection zone 136 and may be utilized to further tailor the characteristics of the device. For instance, upon exposure of the assay device 120 to the test sample, the buffering component can be released and mixed with the test sample to provide the desired pH level for a coupling reaction. When utilizing an indicator reagent that is not reactive with the analyte under normal sample pH conditions, and following release and passage of the buffering agent(s) past the detection zone 136, any additional sample volume that is exposed to the assay device 120 will not generate additional detection signal. Accordingly, the assay device 120 can be provided with an internal test sample volume control, so as to help reduce the likelihood of "false positives," if, for instance, the assay device 120 is exposed to multiple insults of a bodily fluid.

Another zone that may be employed in the lateral flow assay device 120 for improving detection accuracy is a control zone 138. The control zone 138 gives a signal to the user that the test is performing properly. More specifically, reagents may be employed that flow through the chromatographic medium 123 upon contact with a sufficient volume of the bodily fluid being tested. These reagents may then be observed, either visually or with an instrument, within the control zone 138. The control reagents generally contain a detectable substance, such as luminescent compounds (e.g., fluorescent, phosphorescent, etc.); radioactive compounds; visual compounds (e.g., colored dye or metallic substance, such as gold); liposomes or other vesicles containing signal-producing substances; enzymes and/or substrates, and so forth. Other suitable detectable substances may be described in U.S. Pat. No. 5,670,381 to Jou, et al. and U.S. Pat. No. 5,252,459 to Tarcha, et al., which are incorporated herein in their entirety by reference thereto for all purposes.

The control zone 138 may contain a material that is non-diffusively immobilized in the manner described above and forms a chemical and/or physical bond with the control reagents. When the control reagents contain latex particles, for instance, the control zone 138 may include a polyelectrolyte that binds to the particles. Various polyelectrolytic binding systems are described, for instance, in U.S. Patent App. Publication No. 2003/0124739 to Song, et al., which is incorporated herein in it entirety by reference thereto for all purposes. In alternative embodiments, however, the control zone 138 may simply be defined by a region of the absorbent material 154 to which the control reagents flow after traversing through the chromatographic medium 123.

The location of the detection zone 136 and control zone 138 may vary. In the illustrated embodiment, for example, the control zone 138 is defined by the chromatographic medium 123 and positioned downstream from the detection zone 136. This is not a requirement, however, and in another embodiment, the control zone may be upstream of the detection zone.

Regardless of the particular control technique selected and the relative positions of the detection zone and the control zone, the application of a sufficient volume of the test sample to the device 120 will cause a signal to form within the control zone 138, whether or not the analyte of interest is present. Among the benefits provided by such a control zone is that the user or other personnel are informed that a sufficient volume of test sample has been added without requiring careful measurement or calculation. This provides the ability to use the lateral flow assay device 120 without the need for externally controlling the reaction time, test sample volume, etc. In the case of the elderly, children, or patients unable to communicate clearly, control zone 138 provides an indication that a sample was discharged, collected, and successfully tested.

The detection zone 136, control zone 138, reagent zone, or any other zone employed in the lateral flow assay device 120 may generally provide any number of distinct detection regions so that a user may better determine the concentration of the bilirubin or reduction product thereof within the test sample. Each region may contain the same or different materials. For example, the zones may include two or more distinct regions (e.g., lines, dots, etc.). The regions may be disposed in the form of lines in a direction that is substantially perpendicular to the flow of the test sample through the device 120. Likewise, in some embodiments, the regions may be disposed in the form of lines in a direction that is substantially parallel to the flow of the test sample through the device 120.

A lateral flow assay device 120 may optionally include a quenching zone (not shown). A quenching zone is configured to remove compounds from a test sample that would otherwise interfere with the accuracy of the detection system. For example, contaminants within the test sample (e.g., phenolics) or typical levels of the analyte that may be expected in a test sample (e.g., typical bilirubin levels in blood or typical urobilinogen levels in urine) may react with an indicator agent prior to or within the detection zone 136 and form an aromatic azo compound, thereby producing a false result. Thus, a quenching zone may contain a pre-determined amount of a quenching agent, such as a diazonium ion or an Erhlich reagent that is capable of reacting with a typical level of the analyte (e.g., a small amount of urobilinogen in urine for a healthy person) to achieve a zero or near-zero background signal for a negative sample. The quenching reagent in the quenching zone may react with interfering compounds in the sample for the reaction in the detection zone. A quenching agent may be the same or different than the indicator agent used within the detection zone 136. Typically, the quenching agent is non-diffusively immobilized within the quenching zone in the manner described above so that it does not flow through the medium 123 and interfere with testing. The location of the quenching zone may vary, but is typically positioned upstream from the detection zone 136 to avoid interference with detection. For example, in the illustrated embodiment, the quenching zone may be positioned immediately downstream of the sample application zone 142.

In one embodiment, a lateral flow device 120 may include multiple detection zones. For instance, a lateral flow device may include a first detection zone for detection of bilirubin and a second detection zone for detection of urobilinogen to provide a comprehensive examination of a test sample for early detection of jaundice.

In another embodiment, a lateral flow device 120 may include multiple detection zones and multiple reagent zones. For instance, a lateral flow device may include a first detection zone (e.g. with a non-diffusively immobilized diazonium-based indicator) for detection of bilirubin and a second detection zone (e.g., with a non-diffusively immobilized Erhlich reagent-based indicator) for detection of urobilinogen to provide a comprehensive examination of a test sample for early detection of jaundice. A first reagent zone may be located upstream of the first detection zone to provide a certain detection environment (e.g., pH) for the reaction in the first detection zone. A second reagent zone may be located between the first detection zone and the second detection zone to provide a second detection environment (e.g., a different pH, for instance an acidic pH) for the reaction of the second detection zone.

An exemplary method for detecting the presence of urobilinogen within a test sample using the device 120 of FIG. 6 will now be described in more detail. Initially, urine containing urobilinogen is discharged to the sample application zone 142 and travels in the direction "L" to a reagent zone. At the reagent zone, the urobilinogen is able to mix with acid buffers, surfactants, and the like. At the detection zone 136, and in the pH controlled medium, the urobilinogen reacts with a non-diffusively immobilized Erhlich-reagent based indicator to form a colored compound in the detection zone 136. After the reaction, the detection zone 136 changes color. Due to the nature of the controlled fluid flow, any unreacted urobilinogen in the excess urine travels to the end of the reaction medium so that it is unable to adversely interfere with observance of the colored compound in the detection region.

II. Absorbent Article

In accordance with one embodiment, the present disclosure, one or more lateral flow assay devices may be integrated into an absorbent article. An "absorbent article" generally refers to any article capable of absorbing water or other fluids. Examples of some absorbent articles include, but are not limited to, personal care absorbent articles, such as diapers, training pants, absorbent underpants, incontinence articles, feminine hygiene products (e.g., sanitary napkins), swim wear, baby wipes, and so forth; medical absorbent articles, such as garments, fenestration materials, underpads, bedpads, bandages, absorbent drapes, and medical wipes; food service wipers; clothing articles; and so forth. Materials and processes suitable for forming such absorbent articles are well known to those skilled in the art. Typically, absorbent articles include a substantially liquid-impermeable layer (e.g., outer cover), a liquid-permeable layer (e.g., bodyside liner, surge layer, etc.), and an absorbent core.

Various embodiments of an absorbent article that may be formed will now be described in more detail. For purposes of illustration only, an absorbent article is shown in FIG. 1 as a diaper 101. In the illustrated embodiment, the diaper 101 is shown as having an hourglass shape in an unfastened configuration. However, other shapes may of course be utilized, such as a generally rectangular shape, T-shape, or I-shape. As shown, the diaper 101 includes a chassis formed by various components, including an outer cover 117, bodyside liner 105, absorbent core 103, and surge layer 107. It should be understood, however, that other layers may also be used in exemplary embodiments. Likewise, one or more of the layers referred to in FIG. 1 may also be eliminated in certain exemplary embodiments.

The bodyside liner 105 is generally employed to help isolate the wearer's skin from liquids held in the absorbent core 103. For example, the liner 105 presents a bodyfacing surface that is typically compliant, soft feeling, and non-irritating to the wearer's skin. Typically, the liner 105 is also less hydrophilic than the absorbent core 103 so that its surface remains relatively dry to the wearer. As indicated above, the liner 105 may be liquid-permeable to permit liquid to readily penetrate through its thickness. Exemplary liner constructions that contain a nonwoven web are described in U.S. Pat. No. 5,192,606 to Proxmire, et al.; U.S. Pat. No. 5,702,377 to Collier, IV, et al.; U.S. Pat. No. 5,931,823 to Stokes, et al.; U.S. Pat. No. 6,060,638 to Paul, et al.; and U.S. Pat. No. 6,150,002 to Varona, as well as U.S. Patent Application Publication Nos. 2004/0102750 to Jameson; 2005/0054255 to Morman, et al.; and 2005/0059941 to Baldwin. et al., all of which are incorporated herein in their entirety by reference thereto for all purposes.

The diaper 101 may also include a surge layer 107 that helps to decelerate and diffuse surges or gushes of liquid that may be rapidly introduced into the absorbent core 103. Desirably, the surge layer 107 rapidly accepts and temporarily holds the liquid prior to releasing it into the storage or retention portions of the absorbent core 103. In the illustrated embodiment, for example, the surge layer 107 is interposed between an inwardly facing surface 116 of the bodyside liner 105 and the absorbent core 103. Alternatively, the surge layer 107 may be located on an outwardly facing surface 118 of the bodyside liner 105. The surge layer 107 is typically constructed from highly liquid-permeable materials. Examples of suitable surge layers are described in U.S. Pat. No. 5,486,166 to Ellis, et al. and U.S. Pat. No. 5,490,846 to Ellis, et al., which are incorporated herein in their entirety by reference thereto for all purposes.

The outer cover 117 is typically formed from a material that is substantially impermeable to liquids. For example, the outer cover 117 may be formed from a thin plastic film or other flexible liquid-impermeable material. In one embodiment, the outer cover 117 is formed from a polyethylene film having a thickness of from about 0.01 millimeter to about 0.05 millimeter. The film may be impermeable to liquids, but permeable to gases and water vapor (i.e., "breathable"). This permits vapors to escape from the absorbent core 103, but still prevents liquid exudates from passing through the outer cover 117. If a more cloth-like feeling is desired, the outer cover 117 may be formed from a polyolefin film laminated to a nonwoven web. For example, a stretch-thinned polypropylene film may be thermally laminated to a spunbond web of polypropylene fibers.

Besides the above-mentioned components, the diaper 101 may also contain various other components as is known in the art. For example, the diaper 101 may also contain a substantially hydrophilic tissue wrapsheet (not illustrated) that helps maintain the integrity of the fibrous structure of the absorbent core 103. The tissue wrapsheet is typically placed about the absorbent core 103 over at least the two major facing surfaces thereof, and composed of an absorbent cellulosic material, such as creped wadding or a high wet-strength tissue. The tissue wrapsheet may be configured to provide a wicking layer that helps to rapidly distribute liquid over the mass of absorbent fibers of the absorbent core 103. The wrapsheet material on one side of the absorbent fibrous mass may be bonded to the wrapsheet located on the opposite side of the fibrous mass to effectively entrap the absorbent core 103. Furthermore, the diaper 101 may also include a ventilation layer (not shown) that is positioned between the absorbent core 103 and the outer cover 117. When utilized, the ventilation layer may help insulate the outer cover 117 from the absorbent core 103, thereby reducing dampness in the outer cover 117. Examples of such ventilation layers may include a nonwoven web laminated to a breathable film, such as described in U.S. Pat. No. 6,663,611 to Blaney, et al., which is incorporated herein in its entirety by reference thereto for all purposes.

In some embodiments, the diaper 101 may also include a pair of side panels (or ears) (not shown) that extend from the side edges 132 of the diaper 101 into one of the waist regions. The side panels may be integrally formed with a selected diaper component. For example, the side panels may be integrally formed with the outer cover 117 or from the material employed to provide the top surface. In alternative configurations, the side panels may be provided by members connected and assembled to the outer cover 117, the top surface, between the outer cover 117 and top surface, or in various other configurations. If desired, the side panels may be elasticized or otherwise rendered elastomeric by use of an elastic nonwoven composite. Examples of absorbent articles that include elasticized side panels and selectively configured fastener tabs are described in PCT Patent Application WO 95/16425 to Roessler; U.S. Pat. No. 5,399,219 to Roessler et al.; U.S. Pat. No. 5,540,796 to Fries; and U.S. Pat. No. 5,595,618 to Fries, each of which is incorporated herein in its entirety by reference thereto for all purposes.

As representatively illustrated in FIG. 1, the diaper 101 may also include a pair of containment flaps 112 that are configured to provide a barrier and to contain the lateral flow of body exudates. The containment flaps 112 may be located along the laterally opposed side edges 132 of the bodyside liner 105 adjacent the side edges of the absorbent core 103. The containment flaps 112 may extend longitudinally along the entire length of the absorbent core 103, or may only extend partially along the length of the absorbent core 103. When the containment flaps 112 are shorter in length than the absorbent core 103, they may be selectively positioned anywhere along the side edges 132 of diaper 101 in a crotch region 110. In one embodiment, the containment flaps 112 extend along the entire length of the absorbent core 103 to better contain the body exudates. Such containment flaps 112 are generally well known to those skilled in the art. For example, suitable constructions and arrangements for the containment flaps 112 are described in U.S. Pat. No. 4,704,116 to Enloe, which is incorporated herein in its entirety by reference thereto for all purposes.

To provide improved fit and to help reduce leakage of body exudates, the diaper 101 may be elasticized with suitable elastic members, as further explained below. For example, as representatively illustrated in FIG. 1, the diaper 101 may include leg elastics 106 constructed to operably tension the side margins of the diaper 101 to provide elasticized leg bands which can closely fit around the legs of the wearer to reduce leakage and provide improved comfort and appearance. Waist elastics 108 may also be employed to elasticize the end margins of the diaper 101 to provide elasticized waistbands. The waist elastics 108 are configured to provide a resilient, comfortably close fit around the waist of the wearer.

The diaper 101 may also include one or more fasteners 130. For example, two flexible fasteners 130 are illustrated in FIG. 1 on opposite side edges of waist regions to create a waist opening and a pair of leg openings about the wearer. The shape of the fasteners 130 may generally vary, but may include, for instance, generally rectangular shapes, square shapes, circular shapes, triangular shapes, oval shapes, linear shapes, and so forth. The fasteners may include, for instance, a hook-and-loop material, buttons, pins, snaps, adhesive tape fasteners, cohesives, fabric-and-loop fasteners, etc. In one particular embodiment, each fastener 130 includes a separate piece of hook material affixed to the inside surface of a flexible backing.

The various regions and/or components of the diaper 101 may be assembled together using any known attachment mechanism, such as adhesive, ultrasonic, thermal bonds, etc. Suitable adhesives may include, for instance, hot melt adhesives, pressure-sensitive adhesives, and so forth. When utilized, the adhesive may be applied as a uniform layer, a patterned layer, a sprayed pattern, or any of separate lines, swirls or dots. In the illustrated embodiment, for example, the outer cover 117 and bodyside liner 105 are assembled to each other and to the absorbent core 103 using an adhesive. Alternatively, the absorbent core 103 may be connected to the outer cover 117 using conventional fasteners, such as buttons, hook and loop type fasteners, adhesive tape fasteners, and so forth. Similarly, other diaper components, such as the leg elastic members 106, waist elastic members 108 and fasteners 130, may also be assembled into the diaper 101 using any attachment mechanism.

Generally speaking, a lateral flow assay device may be incorporated into the absorbent article in a variety of different orientations and configurations, so long as the device is capable of receiving the bodily fluid and providing a signal to a user or caregiver of the presence or absence of the analyte. For example, the detection zone and/or control zone are normally visible to the user or caregiver so that a simple, accurate, and rapid indication of the presence of the analyte may be provided. The visibility of such zone(s) may be accomplished in a variety of ways. For example, in some embodiments, the absorbent article may include a transparent or translucent portion (e.g., window, film, etc.) that allows the detection zone and/or control zone to be readily viewed without removal of the absorbent article from the wearer and/or without disassembly of the absorbent article. In other embodiments, the detection zone and/or control zone may extend through a hole or aperture in the absorbent article for observation. In still other embodiments, the detection zone and/or control zone may simply be positioned on a surface of the absorbent article for observation.

Referring now to FIGS. 1 and 6, the diaper 101 includes a lateral flow assay device 120 that may be positioned at least partially between the outer cover 117 and the absorbent core 103. The lateral flow assay device 120 may be positioned such that the detection zone 136 and control zone 138 are visible through a window 140 in the outer cover 117. The sample zone 142, positioned at one end of the assay device 120, is strategically positioned in the diaper 101 so that urine discharged by the wearer can travel to the sample zone 142 for collection of at least a portion of the discharged urine therein. The absorbent material 154 is also provided at the other end of the assay device 120 to hold part of the sample and to promote wicking or capillary flow in the device 120 as will be more fully described below.

FIG. 1 illustrates the assay device 120 as being placed directly into the layers that comprise the absorbent article 101. Alternatively, the assay device 120 may be partially or completely encased within a thin film (not shown) except for the sample zone 142, which remains exposed to the bodily fluid (e.g., urine) being tested. Such embodiments may be desirable so as to inhibit other components of the assay device 120, other than the sample zone 142, from receiving the bodily fluid directly from the wearer or from the layers of the absorbent article 101. For example, the assay device 120 may operate more effectively if the absorbent material 154 is shielded so that it draws the bodily fluid only from sample zone 142 and not from the absorbent article 101. Such thin film may be constructed, for example, from a variety of materials including polymers such as polyethylene, polypropylene, polycarbonate, and others.

As stated, the assay device 120 is positioned so as to receive the discharged bodily fluid. As shown, the assay device 120 includes a sample zone 142 for collection of the fluid. Alternatively, the sample zone for assay device 120 may be constructed from one or more components that form parts of the absorbent article 101. By way of example, the sample zone could be constructed as part of the surge layer 107, absorbent core 103, or other components that might be used in the construction of absorbent article 101 and that are capable of receiving and providing fluid to assay device 120.

The assay device 120 may be configured with the diaper 101 in a variety of different placements and orientations. FIG. 1 depicts the assay device 120 at a position between the absorbent core 103 and the outer cover 117. In this manner, the zones 136 and 138 are visible though the window 140 when the diaper 101 is in place on the wearer. The window 140 is made of a transparent material formed as part of the outer cover 117 so as to prevent undesirable leaks of the collected fluids. In such cases, the results of testing with the device 120 may be readily observed without removal of the diaper 101 from the wearer. Alternatively, the device 120 could be placed between, for example, the absorbent core 103 and the bodyside liner 105 with the window 140 being defined by the bodyside liner 105. In such cases, the results of testing with the assay device 120 may be checked when, for example, the diaper 101 is being changed or replaced on the wearer. Furthermore, the device 120 may be placed at other locations and in different orientations as well.

Figure 2:
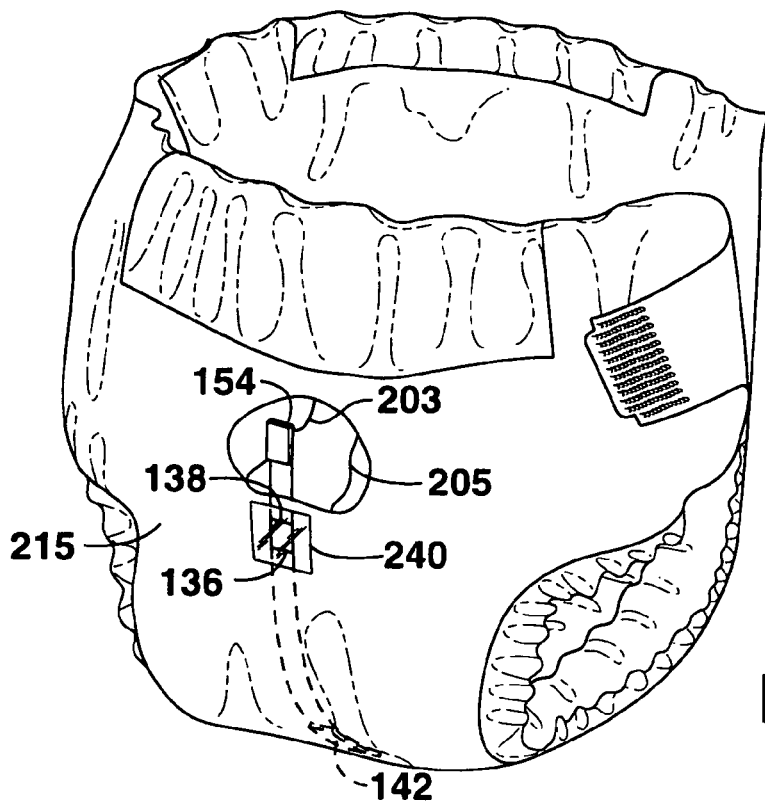
FIG. 2 is perspective view and partial cut-away view of another exemplary embodiment.

In fact, as will be understood using the present disclosure, numerous exemplary embodiments exist for integrating the assay device 120 into an absorbent article as will be further described. For example, FIG. 2 depicts another exemplary embodiment in which the assay device 120 has been integrated into a diaper 215. Here, a window 240 allows observations of the detection zone 136 and the control zone 138 as previously described. Compared to FIG. 1, the assay device 120 has been placed on an opposite side of the diaper 101.

Figure 3:
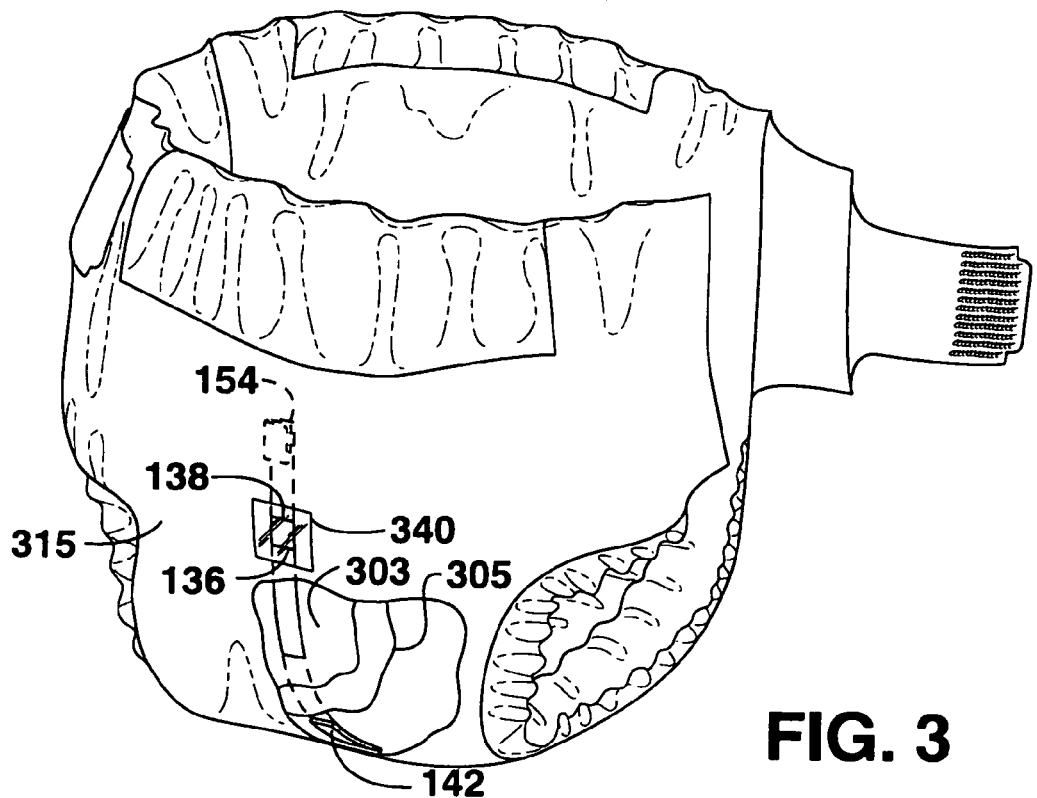
FIG. 3 is perspective view and partial cut-away view of another exemplary embodiment.

FIG. 3 illustrates another exemplary embodiment where the assay device 120 has been integrated into a diaper 315. Again, a window 340 allows observations of the detection zone 136 and the control zone 138 as previously described. In a manner similar to FIG. 1 and FIG. 2, the absorbent material 154 is placed next to the outer cover 117. However, in contrast to FIG. 1 and FIG. 2, the sample zone 142 is placed next to the wearer's skin. More specifically, the diaper 315 is constructed with the assay device 120 extending through absorbent core 303 and body side liner 305 to a position where sample zone 142 will be adjacent the wearer's skin.

Figure 4:
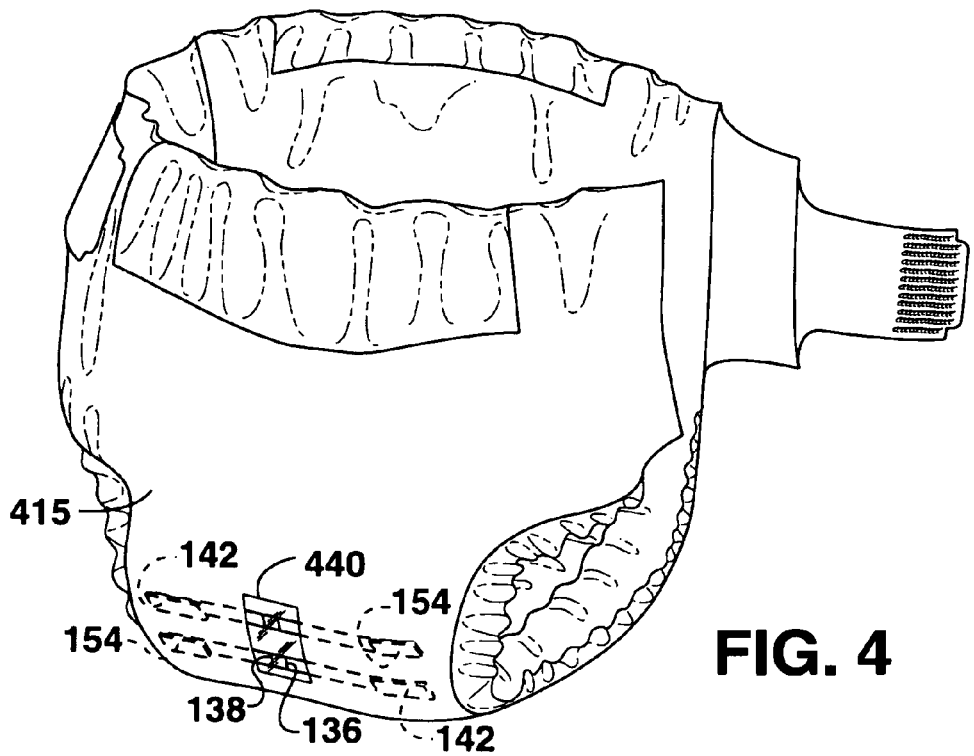
FIG. 4 is perspective view of another exemplary embodiment.

FIG. 4 illustrates a diaper 415 having two assay devices 120 integrated therein. As shown, window 440 allows the detection zone 136 and control zone 138 of two different assay devices 120 to be observed from outside the diaper 415. Such configuration might be desirable, for example, where each assay device 120 is constructed for detecting the presence of different analytes, for instance a first assay device for detection of bilirubin and a second assay device for detection of urobilinogen. In addition, the assays devices in FIG. 4 are oriented at an obtuse angle relative to the embodiments of FIGS. 1 through 3. Thus, FIG. 4 also illustrates that multiple configurations and orientations for devices 120 may be utilized under the teachings disclosed herein.

Figure 5:
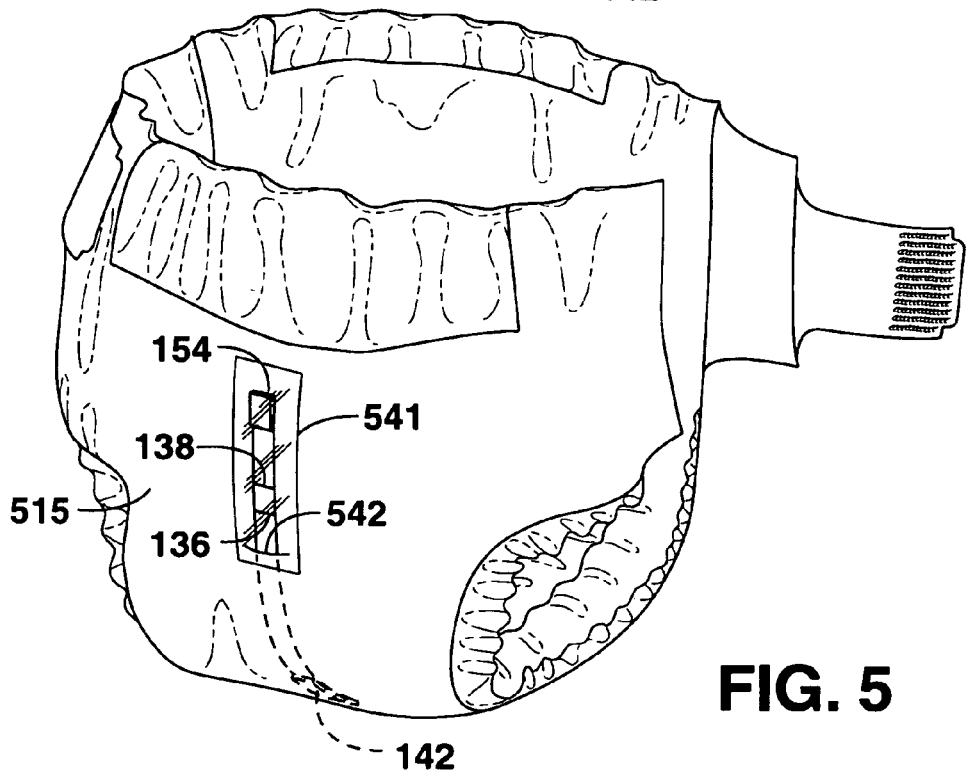
FIG. 5 is perspective view of another exemplary embodiment.

FIG. 5 shows the assay device 120 incorporated into a diaper 515. Rather than being visible through a window, the detection zone 136 and control zone 138 are actually on the outside of the diaper 515. The sample zone 142 resides inside the diaper 515 as part of the assay device 120 and extends through an aperture 542 in a cover 517. A transparent film 541 is affixed to the cover 517 to protect the assay device 120 and prevent fluid leaks from diaper 515.

For each of the embodiments described above, the assay device 120 may be fixed into position in the absorbent article using a variety of techniques or mechanisms. For example, the assay device 120 may be attached using any known attachment mechanism, such as adhesive, ultrasonic, thermal bonds, etc. Suitable adhesives may include, for instance, hot melt adhesives, pressure-sensitive adhesives, and so forth. When utilized, the adhesive may be applied as a uniform layer, a patterned layer, a sprayed pattern, or any of separate lines, swirls or dots. Alternatively, the assay device 120 may be connected using conventional fasteners, such as buttons, hook and loop type fasteners, adhesive tape fasteners, and so forth. By way of further example, pockets or apertures may be built into one or more layers of the absorbent article to fix the position of the assay device 120. In short, a variety of configurations may be used to secure assay device 120 into a position that helps ensure contact with the bodily fluid to be tested.

Again, the embodiments of FIGS. 1 through 6 are provided by way of example only and the present disclosure is not limited to a diaper and may be used with other absorbents articles as well. In addition, numerous configurations and variations of an assay device may be used. Such assay devices may be incorporated in a variety of orientations and configurations into such absorbent articles.

Regardless of the particular manner in which it is integrated, a fluid such as urine may be directly discharged to a portion of chromatographic medium 123, a liquid permeable cover or other material surrounding assay device 120, or may be discharged onto a component of the absorbent article into which the assay device 120 has been integrated. Once the fluid reaches chromatographic medium 123, the fluid may then travel in the direction illustrated by arrow "L" in FIG. 6. Alternatively, the test sample may first be applied to, or supplied to, a sample application zone 142 that is in fluid communication with the chromatographic medium 123. The sample application zone 142 may be formed on the medium 123. Alternatively, as shown in FIG. 1, the sample application zone 142 may be formed by a separate material, such as a pad.

After a sufficient reaction time, the intensity of the color at the detection zone 136 may be measured to quantitatively or semi-quantitatively determine the level of analyte present in the test sample. Nevertheless, while quantitative testing may be performed, qualitative testing is typically employed to provide early testing and monitoring of a health condition. Thus, when bilirubin and/or urobilinogen are visually detected, the user or caregiver is given an indication that further quantitative testing may be undertaken. For example, a diaper having an integrated assay device may be periodically used with infants or non-ambulatory patients as part of a monitoring program that tests for jaundice. Upon indication of a positive test result, further quantitative testing can then be undertaken to determine the scope and stage of the problem detected so a to provide additional treatment information.

The disclosure may be better understood with reference to the examples, set forth below.

EXAMPLE 1

A device including a sample zone, a reagent zone, a detection zone and a wicking zone was formed.

Initially, an Erhlich reagent, diethylaminobenzaldehyde (DEBA) in 0.5 N hydrochloric acid (HCl), was striped on a Millipore HF12002 nitrocellulose membrane card to form a detection zone. The card was then dried at 37° C. for one hour.

A glass fiber pad obtained from Millipore was soaked with oxalic acid (60 mg/ml) and surfactant (Alkanol® S-186) in methanol and dried at 37° C. for one hour to form a reagent zone including both the buffer and the surfactant.

The glass fiber pad was then laminated to one side of the prepared membrane card with an overlap of about 3 mm over the membrane card.

A cellulose pad obtained from Millipore was also laminated onto the same side of the membrane card as glass fiber pad. The cellulose pad was laminated to the membrane card with an overlap of about 3 mm over the membrane card to form a sample zone.

Another cellulose pad was laminated onto the other end of the membrane card with an overlap of about 3 mm with the membrane to form a wicking zone.

The formed card was cut into 5 mm wide strips.

Detection of dimethylindole (DMI) was then carried out with the strips. DMI was used as a simulant for urobilinogen as urobilinogen is not particularly stable. Literature indicates that DMI behaves much like urobilinogen with Erhlich reagents.

To the sample zone of each of seven devices prepared as described above (designated devices 1-7) was added 200 µL aqueous solution including Alkanol® 189-S surfactant containing 0, 1.5, 3, 6, 12, 24, and 48 µg/mL DMI, respectively. After five minutes, a strong pink color line was observed in the detection zone for devices 5, 6, and 7. A moderate pink color line was observed for devices 2, 3, and 4. No pink color line was formed on device 1.

EXAMPLE 2

A detection device similar to that described above in Example 1 was formed, with the exception that the reagent zone did not contain any surfactant. Results obtained were similar to those of Example 1, but pink color formation was much slower.

EXAMPLE 3

A detection device similar to that described above in Example 1 was formed, with the exception that the reagent zone did not contain any buffer. None of the seven devices exhibited any color change in the detection zone.

EXAMPLE 4

A detection device similar to that described above in Example 3 was formed, with the exception that the detection zone contained, in addition to the Erhlich reagent, an oxalic acid (60 mg/mL). Color change was observed for devices 1-6, as described above for Example 1, however, the colors were much weaker and the resulting weaker color change took longer to develop.

It will be appreciated that those skilled in the art, upon attaining an understanding of the foregoing, may readily conceive of alterations to, variations of, and equivalents to these embodiments. Accordingly, the scope of the present disclosure should be assessed as including that of the appended claims and any equivalents thereto.

What is claimed is:

1. A diagnostic test kit for detecting the presence or amount of at least one of bilirubin and urobilinogen within a test sample, the diagnostic test kit comprising:
a lateral flow assay device, the lateral flow assay device including:
a chromatographic medium defining a detection zone within which an indicator reagent is non-diffusively immobilized, wherein the indicator reagent is capable of reacting with bilirubin or urobilinogen to generate a detection signal, wherein a reagent zone is positioned upstream from the detection zone within which is diffusively immobilized a component that facilitates the reaction of the indicator reagent with bilirubin or urobilinogen; and
an absorbent material that receives the test sample after flowing through the chromatographic medium.

2. The diagnostic test kit of claim 1, wherein the indicator reagent is a diazonium salt or a derivative thereof.

3. The diagnostic test kit of claim 2, wherein the diazonium salt is p-aminobenzenesulfonic acid, 2,6-dichlorobenzene diazonium tetrafluoroborate, or 2-trifluoromethylbenzene diazonium.

4. The diagnostic test kit of claim 2, wherein the diazonium salt is 4-fluoro-3-nitrobenzenediazonium salt, 4-methoxy-benzene-diazonium-tetrafluoroborate, or 3,3'-dimethoxybiphenyl-4,4'-diazonium salt.

5. The diagnostic test kit of claim 1, wherein the indicator reagent is an Erhlich reagent or a derivative thereof.

6. The diagnostic test kit of claim 1, wherein the indicator reagent comprises a macromolecular moiety and a reactive moiety.

7. The diagnostic test kit of claim 6, wherein the macromolecular moiety is formed from a polymer.

8. The diagnostic test kit of claim 7, wherein the polymer is a polysaccharide.

9. The diagnostic test kit of claim 6, wherein the macromolecular moiety is formed from a particle.

10. The diagnostic test kit of claim 9, wherein the particle is a carboxylated latex particle.

11. The diagnostic test kit of claim 1, wherein the chromatographic medium is a porous membrane.

12. The diagnostic test kit of claim 1, further comprising a sample application zone that is located upstream from the reagent zone.

13. The diagnostic test kit of claim 1, further comprising a quenching zone located upstream from the detection zone.

14. The diagnostic test kit of claim 1, further comprising a control zone that is capable of signaling the presence of the test sample.

15. The diagnostic test kit of claim 14, further comprising a control reagent that is capable being detected within the control zone.

16. The diagnostic test kit of claim 1, wherein the test sample is urine.

17. The diagnostic test kit of claim 1, wherein the indicator reagent preferentially reacts with bilirubin to generate the detection signal.

18. The diagnostic test kit of claim 1, the lateral flow assay device further comprising a second detection zone within which a second indicator reagent is immobilized, wherein the second indicator reagent preferentially reacts with urobilinogen to generate a second detection signal.

19. The diagnostic test kit of claim 18, the lateral flow assay device further comprising a second reagent zone which is located down stream of the first detection zone and upstream of the second detection zone.

20. An absorbent article for receiving a bodily fluid suspected of containing bilirubin or urobilinogen, comprising:
a substantially liquid impermeable layer;
a liquid permeable layer;
an absorbent core positioned between the substantially liquid impermeable layer and the liquid permeable layer; and
a lateral flow assay device integrated into the article and positioned such that the device is in fluid communication with the bodily fluid when provided by a wearer of the article, the lateral flow assay device comprising a chromatographic medium that defines a first detection zone in which a first indicator reagent is non-diffusively immobilized, the first detection zone being configured for exhibiting a signal indicative of the presence or amount of at least one of bilirubin and urobilinogen in the bodily fluid, wherein a reagent zone is positioned upstream from the detection zone within which is diffusively immobilized a component that facilitates the reaction of the indicator reagent with bilirubin or urobilinogen.

21. The absorbent article of claim 20, wherein the lateral flow assay device includes a control zone for indicating that a sufficient volume of the bodily fluid has been received by the lateral flow assay device.

22. The absorbent article of claim 20, further comprising a control reagent that is capable of being detected within the control zone.

23. The absorbent article of claim 20, wherein the absorbent article defines a window through which the detection zone, the control zone, or both is observable.

24. The absorbent article of claim 20, wherein the lateral flow assay device further comprises a sample application zone.

25. The absorbent article of claim 24, wherein the sample application zone is comprised of at least part of the absorbent core.

26. The absorbent article of claim 20, wherein the lateral flow assay device is positioned between the substantially liquid impermeable layer and the absorbent core.

27. The absorbent article of claim 20, wherein the lateral flow assay device is positioned between the liquid permeable layer and the absorbent core.

28. The absorbent article of claim 20, wherein the first indicator reagent is a diazonium ion or a derivative thereof.

29. The absorbent article of claim 20, wherein the first indicator reagent is an Ehrlich reagent or a derivative thereof.

30. The absorbent article of claim 20, wherein the first indicator reagent comprises a macromolecular moiety and a reactive moiety.

31. The absorbent article of claim 20, wherein the detection zone is configured to exhibit a signal indicative of the presence or amount of bilirubin in the bodily fluid.

32. The absorbent article of claim 31, wherein the lateral flow device further comprises a second detection zone, the second detection zone comprising a second indicator reagent, wherein the second detection zone is configured to exhibit a signal indicative of the presence or amount of urobilinogen in the bodily fluid.

33. The absorbent article of claim 20, wherein the absorbent article is a diaper.

34. The absorbent article of claim 33, wherein the diaper further comprises a second lateral flow assay device integrated into the article and positioned such that the second lateral flow assay device is in fluid communication with the bodily fluid when provided by a wearer of the article, the second lateral flow assay device comprising a porous membrane that defines a second detection zone, the second detection zone comprising a second indicator reagent, the second lateral flow assay device being configured for exhibiting a signal indicative of the presence or amount of at least one of bilirubin and urobilinogen in urine.

35. A method of detecting the presence or amount of at least one of bilirubin and urobilinogen within a bodily fluid, the method comprising:
providing a lateral flow assay device, the lateral flow assay device comprising a chromatographic medium that defines a first detection zone in which a first indicator reagent is non-diffusively immobilized, the first detection zone being configured for exhibiting a signal indicative of the presence or amount of at least one of bilirubin and urobilinogen in the bodily fluid, wherein a reagent zone is positioned upstream from the detection zone within which is diffusively immobilized a component that facilitates the reaction of the indicator reagent with bilirubin or urobilinogen;
contacting the lateral flow assay device with the bodily fluid; and
observing the detection zone for the visual detection signal.

36. The method of claim 35, further comprising quantitatively or semi-quantitatively testing for the bilirubin or urobilinogen after the visual detection signal is observed.

37. The method of claim 35, wherein the bodily fluid is urine.

38. The method of claim 35, wherein the lateral flow assay device is disposed within an absorbent article.

39. The method of claim 38, wherein the absorbent article is a diaper.

40. The method of claim 35, wherein the detection zone is configured to provide a visual detection signal indicative of the presence or absence of bilirubin within the bodily fluid.

41. The diagnostic test kit of claim 1, wherein the reagent zone is defined by a reagent pad in fluid communication with the chromatographic medium.

42. The diagnostic test kit of claim 1, wherein the component is a buffer, surfactant, or a mixture thereof.

43. The diagnostic test kit of claim 42, whereon the component includes an acidic buffer.

44. The absorbent article of claim 43, whereon the component includes an acidic buffer.

45. The method of claim 35, wherein the component is a buffer, surfactant, or a mixture thereof.

46. The method of claim 45, whereon the component includes an acidic buffer.

47. The absorbent article of claim 20, wherein the component is a buffer, surfactant, or a mixture thereof.

* * * * *

UNITED STATES PATENT AND TRADEMARK OFFICE
CERTIFICATE OF CORRECTION

| | |
|---|---|
| PATENT NO. | : 7,846,383 B2 |
| APPLICATION NO. | : 11/640116 |
| DATED | : December 7, 2010 |
| INVENTOR(S) | : Xuedong Song |

Page 1 of 1

It is certified that error appears in the above-identified patent and that said Letters Patent is hereby corrected as shown below:

On the title page item (56), Under References Cited - U.S. Patent Documents the following reference needs to be added:

RE38430   02/2004   Rosenstein

Signed and Sealed this
Fourth Day of October, 2011

David J. Kappos
*Director of the United States Patent and Trademark Office*